United States Patent
McCarty

(12) 
(10) Patent No.: US 6,231,502 B1
(45) Date of Patent: May 15, 2001

(54) IMPOTENCE CONSTRICTION RING AND SEAL

(76) Inventor: Donald Lewis McCarty, P.O. Box 1558, Julian, CA (US) 92036

( * ) Notice: Subject to any disclaimer, the term of this patent is extended or adjusted under 35 U.S.C. 154(b) by 0 days.

(21) Appl. No.: 09/293,652

(22) Filed: Apr. 17, 1999

Related U.S. Application Data

(63) Continuation-in-part of application No. 08/980,857, filed on Nov. 29, 1997, now abandoned, which is a continuation-in-part of application No. 08/847,576, filed on Apr. 24, 1997, now abandoned, which is a continuation-in-part of application No. 08/413,842, filed on Mar. 30, 1995, now Pat. No. 5,647,837.

(51) Int. Cl.[7] .......................................................... A61F 5/00
(52) U.S. Cl. .................................................................. 600/38
(58) Field of Search ........................................... 600/38–41

(56) References Cited

U.S. PATENT DOCUMENTS

| | | | |
|---|---|---|---|
| 3,759,253 | * | 9/1973 | Cray ........................................ 600/38 |
| 5,246,015 | * | 9/1993 | Baber ..................................... 128/842 |
| 5,306,227 | * | 4/1994 | Osbon et al. ............................ 600/41 |
| 5,344,389 | * | 9/1994 | Walsdorf et al. ....................... 600/41 |
| 5,460,594 | * | 10/1995 | Walling ................................... 600/38 |
| 5,468,211 | * | 11/1995 | Welch ..................................... 600/38 |
| 5,628,329 | * | 5/1997 | Bennett et al. ....................... 128/842 |
| 5,695,444 | * | 12/1997 | Chaney .................................. 600/38 |

* cited by examiner

Primary Examiner—Samuel G. Gilbert

(57) ABSTRACT

A device and method to aid in male potency by producing and maintaining an erection by means of using a vacuum device with inflatable sliding seals to establish and maintain a vacuum, providing the operator time to install a retaining device on his penis in an area of his choice. The sliding inflatable seals preclude the necessity of creating a vacuum seal against the groin area with its ensuing problems of scrotum and abdominal tissue ingestion. The Restrictor Seal incorporates differential pressure pad areas to selectively place pressure on specific areas of the penis to optimize incoming blood flow and restrict outgoing blood flow required to maintain the erection, by means of which erections can be maintained longer, and with less opportunity of a degraded thermal loss of the penis. Seminal ejaculation is effected by means of a urethra relief groove. The deflation of the seals in the device create a means of easy removal of the device from the penis without pain or discomfort or penile tissue damage.

5 Claims, 2 Drawing Sheets

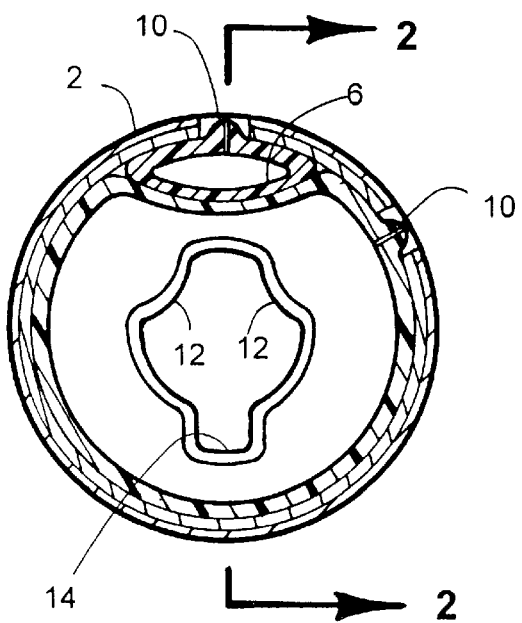
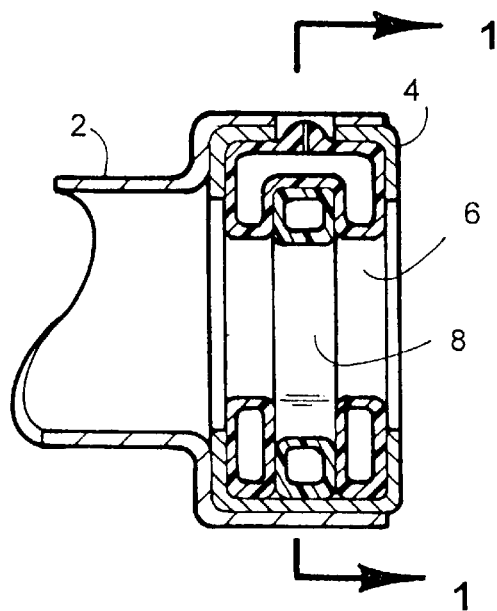
FIGURE 1
figure 2
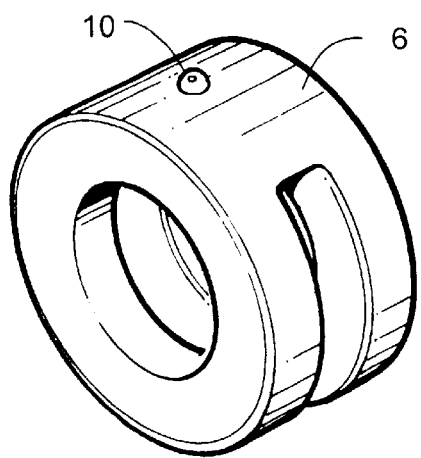
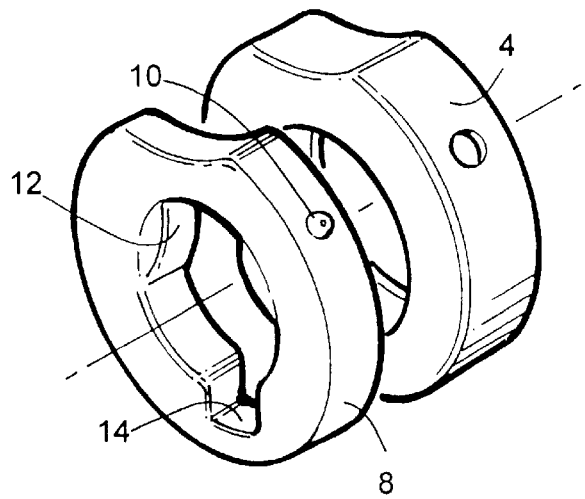
Figure 3
Figure 4

IMPOTENCE CONSTRICTION RING AND SEAL

CROSS-REFERENCES TO RELATED APPLICATIONS

Heading for Conditions for Domestic Priority Under U.S.C. 119(e)

This is a Continuation In Part of U.S. application Ser. No. 08/980,857 filed Nov. 29, 1997 now abandoned; which is a Continuation In Part of U.S. application Ser. No. 08/847, 576, filed Apr. 24, 1997, now abandoned which is a Continuation In Part of 08/413,842 filed Mar. 30, 1995, now U.S. Pat. No. 5,647,837.

STATEMENT REGARDING FEDERALLY SPONSORED RESEARCH OR DEVELOPMENT

Not Applicable.

REFERENCE TO A "CROFICHE APPENDIX"

Not Applicable

BACKGROUND OF THE INVENTION

1. Field of the Invention

Impotency is a major problem for millions of men. It is the result of a multitude of problems including circulation deficits from debilitating diseases such as diabetes and cancer, spinal injury, aging, and the adverse cross-effects of medication. Impotency drastically effects and reduces the standard of life of the partners to a marriage, by increasing stress on couples already burdened with ill health and aging.

2. Description of the Related Art including information disclosed under 37 CFR 1.97 and 1.98.

(1) Prior Art

Therapy for impotency has been treated for many years by herbs, drugs and mechanical devices. Numerous types of herbs and prescription drugs apply a systemic chemical stimulation to effect the flow and retention of blood in the penis to effect an erection. Vacuum Erection Devices draw blood into the penis, where it is retained by a constriction device to attain and retain an erection of the penis (2) Deficiencies in the Art Herbs and natural remedies have historically not provided a consistent success rate for providing relief from impotence; some herbs can produce dangerous side effects with other herbs and drugs.

Prescription drugs attack the problem by a systemic application of chemicals which are invasive per se; they can negatively interact with other medication, and may be dangerous to use for patients with certain health risks. They are convenient for the patient to use; however the health risk of the use of one such prescribed drug for impotence has been attributed to approximately 200 deaths in its early years of use.

Surgically Implanted Mechanical Devices have provided comfort for men who experience erectile dysfunction; however they are very invasive, they can create permanent tissue damage, and a loss of sensitivity, as well as the risk of surgery per se.

Prior State of the Art Vacuum Erection Devices are awkward for the patient to use, however they are non-evasive and therefore are not life threatening. They have the advantage of not being a systemic application of a therapy which requires of a specifically designed target.

Full advantage of Vacuum Erection Devices concepts have not been refined to fully utilize the anatomy of the penile arteries which are located in the central portion of the penis, and the veinal vessels are located sub-dermally to the penis. Arterial blood flow is induced into the flaccid penis when it is inserted in a vacuum plenum, the a constricting ring, which is essentially a tourniquet, is used to restrain the veinal blood flow from leaving the penis to retain the erection. Differential pressures on the penile arteries, veinal vessels and adjacent tissue must be applied to the penis in such a manner to optimize maximum erection time while maintaining a healthy blood flow control in the penis; provisions also be must be included to eliminate occlusion of seminal ejaculation.

Prior Art has been awkward, and as such patients are reluctant to use it for continued therapy; refining the design of Vacuum Erection Devices give the patient an alternative to avoiding more risky invasive therapy.

Cray, U.S. Pat. No. 3,759,253; makes no claim for urethra clearance to effect ejaculation, and it makes no provision or claims to retain said urethra clearance when the device is stretched and distorted when under tension whereby it loses it's geometric shape when applied to an turgid penis, and thereby loses it effect of clearance for ejaculation relief when it is used as a constricting device to control blood flow in the penis.

Hale, U.S. Pat. No. 5,336,157; is not fully compatible with a Vacuum Erection Device use; it lacks ability to optimally control veinal vessel and penile arteries blood flow; it could produce damage to penile tissue, and be an irritant to partner's vagina and pubic hair.

Kock, U.S. Pat. No. 4,203,432; this device is not capable of being assembled optimally on the penis to be used in conjunction with a Vacuum Erection Device; it makes no claims for urethra clearance obstruction to effect ejaculation; it can produce damage to penile tissue and can be intrusive to partner's vagina and pubic hair.

Yanuck, U.S. Pat. No. 4,753,227; omits claims or provisions for the application of differential pressure to control blood flow to effect an erection; it also omits claims or provisions for ejaculation relief Yamanaka, U.S. Pat. No. 5,234,401; employs a method to achieve an erection, but omits addressing the problem of adequately retaining the erection, or providing for ejaculation relief.

Osborn, U.S. Pat. No. 5,234,402; is not a workable solution in that the flat disc-like tissue shield is awkward for the patient to apply, and in that it is part of the cincture band it lacks flexibility and mobile ability to conform to the change in size of the flaccid penis without loss of vacuum which is required to effect an erection; it does not address differential pressure requirements between the penile arteries and veinal vessels to control blood flow to produce an optimum erection; and the device's limited function as a cincture band can make it difficult and painful to remove from an engorged penis.

Walsdorf, U.S. Pat. No. 5,344,389; lacks the ability to seal properly without loss of vacuum due to the increase diameter of the penis as it changes from a flaccid state to a turgid state, it does not selectively control penile and veinal blood flow for optimal erection, it does not make provisions for protection of the seminal vesicular tube or urethra of the penis for ejaculatory relief, and it can be awkward for the patient to apply, and painful and difficult to remove from a turgid penis.

Merrill et al, U.S. Pat. No. 5,125,890; does not claim or employ any means of relieving pressure of a stricture on the seminal vesicular tube or urethra of the penis for ejaculation relief; it does not claim or employ any means of creating differential pressure on the erect penis to control or sustain an optimal erection of the penis.

Osborn, U.S. Pat. No. 5,244,453; does not claim or address that the "cincture band" it uses as a tourniquet can or is able to create differential pressure on the penis to control blood flow in the penis, nor does it claim or address solution of occlusion of the seminal urethra tube for ejaculation; it can difficult and painful to remove from a turgid penis.

Baber, U.S. Pat. No. 5,246,015; makes a provision for clearance and avoidance of occlusion of the penile urinary tract; it does not produce required blood flow into the penis, nor does it make adequate provision for differential blood flow in the penis, nor is the design suitable for utilizing Vacuum Erection Devices; it lacks ability to conform to the growth of the diameter of the penis because of the integral combination of the "annular rim" and the "tubular portion", it lacks stability and could be a irritant to the user and his sex partner, in that "Should the device slide forward . . . the thrust from the sex act will force the device . . . back to its proper position", the device's ability to correct an impotence problem is less than marginal at best, as it's application to a flaccid penis as claimed, acts as a deterrent to the infusion of needed blood into the penis which is required for it's erection; in the event a erection could be achieved while the device encircled the penis, the device could produce difficulty and pain of it's removal from a turgid penis.

Osborn U.S. Pat. No. 5,306,227; cannot retain its geometric shape when it is stretched to go over an erect penis; therefore any groove or channel designed to provide urethra clearance to protect for urethra occlusion which exists in it's geometry in a state of rest disappear and is non-functional and becomes moot in it's intended to the role as a tourniquet to restrict from flow when stretched and applied to an erect penis; no claim or provision is made for selective differential pressure of the retaining ring on an erect penis to optimize blood flow to extend duration of user's wear or counteract diminished temperature gradients in the penis.

Finkle, U.S. Pat. No. 5,338,288; is an effective primitive tourniquet which does not claim or provide for differential control of blood flow in an erect penis, nor eliminate occlusion to the urethra for seminal ejaculation; it could be difficult and painful to remove from a turgid penis by the patient.

Collins, U.S. Pat. No. 5,370,601; does not claim or employ a means of inducing blood flow into the penis to create an erection, no claim or means are addressed to creating or maintaining a differential blood flow control in the penis, and no provision is made for occlusion of the urethra in the device, it could be extremely difficult and painful for the patient to remove it from a turgid penis.

Chaney, U.S. Pat. No. 5,695,444; does not employ a vacuum device and lacks the ability to bring significant blood flow into the penis to achieve an acceptable erection; it could be non-functional on most patients exhibiting significant erectile dysfunction; it could be extremely difficult to apply over the genitals and scrotum, and even more difficult to remove from the genitals with an erect penis making it unsuitable for many patients.

McCarty, U.S. Pat. No. 5,647,837; is a significant advancement, in that it creates a vacuum seal on the flaccid penis, and maintains said seal while the penis achieves it erectile state, so that no vacuum loss occurs and the erection is not compromised in applying a constriction device for blood flow control; but the invention does not address differential pressure points or urethra clearance for ejaculation.

McCarty, application Ser. No. 08/647,576 is a continuation in part of U.S. Pat. No. 5,647,837; it addresses urethra clearance for ejaculation, but dose not address differential pressure points for specific blood flow control.

BACKGROUND OF INVENTION

The present invention concentrates on a specific non-invasive therapy for impotence for those patients who can not tolerate an invasive remedy, and thereby advances the art in Vacuum Erection Device therapy.

The function of a natural erection of the penis requires basically two essential physical steps, namely entry of blood into the penis via the penile arteries, and retention of the blood via constriction of the veinal vessels to engorge the sponge like structure containing cavernous spaces for occupied blood, while maintaining and inducing a sufficient blood flow to the penis; the penis as an organ is dependent on an erectile state to supply it with a significant amount of oxygen, nutrients and chemicals that it normally receives in several hours of nocturnal erections.

Inadequate blood flow is sensed in the erect penis by symptoms of coldness of the penis, display of dark colors and lack and change of sensitivity. Periodic use of a properly designed Vacuum Erection Device can induce a healthy blood flow into the penis to compensate for natural losses because of circulatory problems, and thus reduce atrophy of the penis.

This invention uses a means whereby a vacuum plenum is provided in which the flaccid penis is inserted, and sealed near its base with a flexible seal to accommodate the change in size and shape of the penis, a vacuum is employed on the penis per se to induce blood flow into the penile arteries to engorge the sponge like structure containing the cavernous spaces via the veinal vessels.

The penile arteries are essentially located within the central area of the penis; and the veinal vessels which serve the cavernous spaces, which are drained of blood by small flow restricting veins, are located essentially on the outer surface of the penis.

This invention utilizes said anatomy of the penis to provide differential pressure on the erect penis to promote maximum blood circulation, maintain higher thermal gradients of the penis, and provide clearance for the urethra so as not to occlude seminal ejaculation; one version uses a re-enforced restraining ring with provisions for differential pressure on the penis and urethra clearance; while a companion design incorporates dual inflatable chambers, wherein the combination Primary Bladder Seal and Secondary Restrictor Seal are arranged such that differential pressures can be maintained on specific areas of the penis to optimize the inflow of blood, and concurrently restrict its drainage in other distinct areas, thus effecting a more efficient significant erection of the penis in size and duration. Provisions of this invention include provisions for Urethra Seminal Clearance for ejaculation relief. One version of this invention improves upon the old style snap-on tourniquet retaining ring, and also provides a more comfortable and efficient version that is deflatable for easy application and removal.

BRIEF DESCRIPTION OF THE SEVERAL VIEWS OF THE DRAWINGS

FIG. 1. is a end section view of the assembly of the Primary Bladder Seal number 6, and Secondary Restrictor Seal number 8 assembled in Assembly Housing number 4, inserted in Vacuum Cylinder number 2.

FIG. 2. is a cross section view of the embodiments as depicted in FIG. 1.

FIG. 3. is an isometric view of Primary Bladder Seal number 6, showing Valve number 10

FIG. 4. is an isometric view of Secondary Seal number 8, showing valve number 10, Selective Pressure Pads number 12, and Urethra Seminal Relief Channel number 14; and Assembly Housing number 4

DETAILED DESCRIPTION OF THE INVENTION

Figure 5:
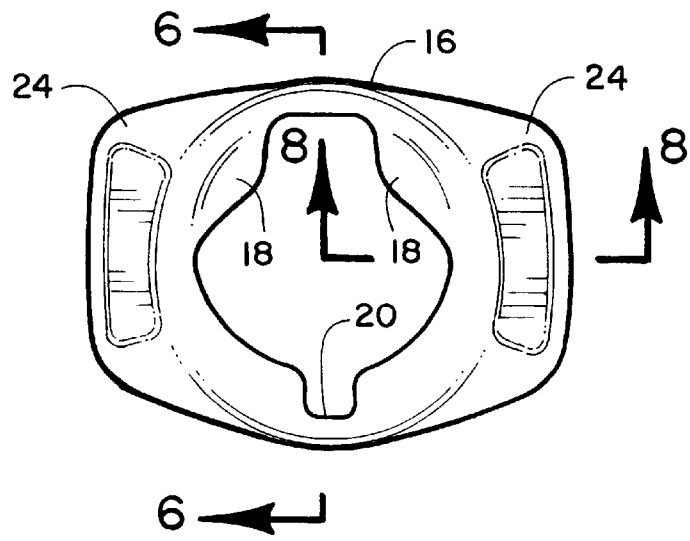
FIG. 5. is a front view of Constriction Ring number 16, showing Differential Pressure Pads number 18, Urethra Seminal Relief Channel number 20, and Removal Tabs number 24.

FIGS. 1 and 2 show the assembly of the inflatable Impotence Constriction Ring and Seal; it consists of an Assembly Housing number 4, which contains a Primary Bladder Seal Number 6, and a Secondary Restrictor Seal Number 8, all of which are assembled in the end of Vacuum Cylinder number 2.

The Assembly Housing, Number 4, is essentially a bezel constructed of rigid, semi ridged plastic or elasatomer, which holds the Primary Bladder Seal Number 6, and Secondary Restrictor Seal Number 4, in place when they are in an inert state, and also when said seals are pressurized. The outside diameter of the Assembly Housing is of such diameter that it makes a slip fit for its containment in the end of Vacuum Cylinder Number 2, with sufficient tolerances to assure a low P.S.I vacuum seal.

The Primary Bladder Seal and Secondary Restrictor Seal are constructed of a flexible elastomer with sufficient memory to recover to their original dimensions after being pressurized to a low P.S.I. Any suitable synthetic elastic material can be used.

The Primary Bladder Seal, Number 6, has an inside diameter to accommodate a slip fit over a flaccid penis, and incorporates a Valve, Number 10, which allows for controlled pressurization and deflation of said Primary Bladder Seal.

The Secondary Restrictor Seal Number 8, is also constructed of a similar material to that of the Primary Bladder Seal, and also incorporates a Valve, Number 10, which allows for its controlled pressurization and deflation. The Secondary Restrictor Seal contains Selective Pressure Nodules, Number 12, and Urethra Seminal Relief Channel, Number 14.

The Selective Pressure Pads are protrusions on the inside diameter of the Secondary Relief Seal that extend from its inside diameter, and are of such dimension that they are in contact with and indent the outside diameter of the penis in an erect state.

The Urethra Seminal Relief Channel Number 14, as shown in FIGS. 1,2, and 4, is a groove on the lower inside diameter of the Secondary Restrictor Seal Number 8 with dimensions necessary to give adequate clearance for the urethra of the penis.

The Impotence Constriction Ring and Seal is employed by means of assembling the device into the end of a Vacuum Cylinder Number 2, and inserting the flaccid penis into it; then by means of a pneumatic pressure device a sufficient minimum pneumatic pressure is applied into the Primary Bladder Seal number 6 so as to create a vacuum seal around the penis while the device is contained in the Vacuum Cylinder; this is followed by employing a vacuum pump which creates a sufficient vacuum in the vacuum chamber to effect the desired size of the erection of the penis. At this stage The Secondary Restrictor Seal number 8 is then pressurized by means of a pneumatic pressure device to the extent that it creates a significant pressure necessary to act as a Selective Pressure Pad on the veinal vessels and sponge like structure containing cavernous spaces for occupied blood, while at the same time permitting an optimal flow of blood to the penis.

The Selective Pressure Pads number 12, are an integral part of the Secondary Restrictor Seal number 8 and its protrusions make selective pressure on the veinal vessels and the sponge like structure containing cavernous spaces for occupied blood, while simultaneously relieving pressure on the penile arteries so as to induce more inbound blood into the penis, to minimize coldness of the penis exhibited by some patients because of lack of blood circulation, and increase the effective time the Secondary Restrictor Seal may be kept in place.

The Primary Bladder Seal Number 6 is then depressurized by means of Valve Number 10, so as not to confound the function of the Secondary Restrictor Seal Number 8.

The vacuum in the Vacuum Cylinder Number 2 is the evacuated, and the Device is then removed from the Vacuum Cylinder, where it is left in place on the penis to retain the erection making the erect penis available for sexual activity.

To remove the device from the penis, the Secondary Restrictor Seal is simply deflated by Valve Number 10, and the Device is easily removed from the penis.

Figure 6:
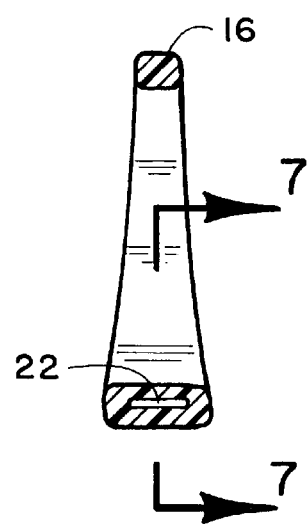
FIG. 6. is a cross section view of the embodiments as depicted in FIG. 5, showing Reinforcement Brace number 22.
Figure 7:
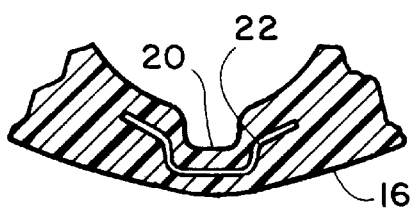
FIG. 7. is a cross section view of the embodiments as depicted in FIG. 6, showing Urethra Seminal Relief Channel number 20, and Reinforcement Brace number 22.
Figure 8:
FIG. 8 is a cross section view of the embodiments as depicted in FIG. 5, depicting a cross section view of Removal Tabs number 24.
Figure 9:
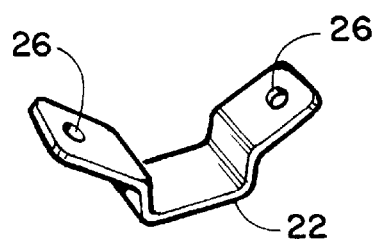
FIG. 9 is an isometric view of the Reinforcement Brace number 22, as depicted in FIGS. 6 and 7, showing Index Alignment Holes or Slots number 26.

FIGS. 5 through 9 show embodiments of the solid core version of the Impotence Constriction Ring, the body of ring number 16 is made of one of the many elastomers which contain a high memory level factor; it contains a Reinforcement Brace number 22 which is made from spring metal or high strength polymers to maintain it's rigid geometric shape of the Urethra Seminal Relief Channel number 20, which contains indexing holes or slots number 26, for alignment and inclusion of it when manufacturing it within the molds for the constriction of Constricting Ring body number 16; the internal diameter of the Constricting Ring body number 16 contains Differential Pressure Pads number 18, which are pronounced protudences by means of which selective pressure areas are presented against the outside diameter of the erect penis; Removal Tabs number 24 are located on the outboard side of the body of Constricting Ring number 16 in such a manner that by means of their geometry they distribute the internal load evenly in an outerly radial direction with minimal internal distortion of the inside diameter of the Constriction Ring when it is removed from an erect penis.

This invention of the inflatable model of the Impotence Constriction Ring and Seal have advantages over the older styles of solid core elastic tourniquets which where employed by being snapped on to the penis, causing pain and uncomfortable, and leading to tissue injury. It is also a dramatic improvement for the act of removal of the constricting ring from the engorged erect penis after sexual activity, by eliminating pulling off the constricting ring from the penis, which tends to push engorged blood towards the end of the penis which enlarges the end of the penis the patient is attempting to avoid, creating pain and tissue trauma in the process.

For those patients who can tolerate the solid elastomer constriction ring, a version of the invention advances the art by improved geometry for maximum control and flow of blood circulation the erect penis, the stable urethra seminal relief channel assures that their is no occlusion of the seminal urethra, and geometric design of it's removal tabs allows for easier removal from a turgid penis.

For patients that are able to achieve an initial erection and are then unable to retain it for a significant duration, the invention may be used without use of the vacuum apparatus, to maintain and control the erection.

This invention further refines the art of Vacuum Erection Devices, to make them easier and more comfortable for the patient to use. This allows the patient a broader choice of therapy which is non-evasive, non-life threatening from cross effects of other medications and health problems, and much less expensive.

It is hereby claimed:

1. A device for implementing and maintaining an erection of the penis comprising;

an elongated tubular vacuum cylinder plenum, containing a primary bladder seal and secondary restrictor seal composed of an elastomer with self restoring memory such that the seals maintain their basic geometric shape during a duty cycle, the seals are assembled in an assembly housing having an open end defining a chamber that is adapted to receive to a flaccid penis;

means for inflating the primary bladder seal to seal the penis and vacuum cylinder plenum from outside ambient air pressure;

means connected to the vacuum cylinder plenum for evacuating ambient atmospheric air pressure from said vacuum cylinder plenum to induce the flow of blood into the penis inserted therein to effect an erection of the penis;

means for inflating the secondary restrictor seal to selectively constrict and control blood flow in the penis;

a first valve connected to the primary bladder seal for decompressing the primary bladder seal to ambient atmospheric pressure;

said assembly housing being selectively removable form the vacuum cylinder plenum;

a second valve connected to the secondary restrictor seal for decompressing the secondary restrictor seal to ambient atmospheric pressure and;

wherein the primary bladder seal and secondary restrictor seal are selectively removable from the assembly housing and when removed the secondary restrictor seal functions as a constriction ring.

2. The device as recited in claim 1, wherein first and second valves includes means defining an aperture through the wall of the seals providing for pressuring the internal area of said seal to above ambient atmospheric pressure, and means for reducing said internal pressure to ambient atmospheric pressure.

3. The device as recited in claim 2, wherein said first and second valves are independent of each other and may selectively pressurize either seal independently.

4. The device as recited in claim 3, wherein the secondary restrictor seal includes pressure pads for inducing pressure areas on specific areas of the penis.

5. The device as recited in claim 4, wherein the secondary restrictor seal includes a urethra seminal relief channel to facilitate the ejection of seminal fluids.

* * * * *